United States Patent [19]

Kuyama et al.

[11] 4,384,881
[45] May 24, 1983

[54] HERBICIDALLY ACTIVE NOVEL BENZAZOL-2-YLOXYACETANILIDES

[75] Inventors: Shinpei Kuyama; Masahiro Aya; Junichi Saito, all of Tokyo, Japan

[73] Assignee: Nihon Tokushu Noyaku Seizo K.K., Tokyo, Japan

[21] Appl. No.: 362,574

[22] Filed: Mar. 26, 1982

[30] Foreign Application Priority Data

Apr. 6, 1981 [JP] Japan ................................... 56-50562

[51] Int. Cl.³ ................. G07D 263/58; G07D 277/68; A01N 43/76
[52] U.S. Cl. ........................................... 71/88; 71/90; 548/171; 548/221
[58] Field of Search ..................... 548/171, 221; 71/88, 71/90

[56] References Cited

FOREIGN PATENT DOCUMENTS 5501 11/1979 European Pat. Off. ................ 71/90
37524 10/1981 European Pat. Off. ................ 71/90

Primary Examiner—Robert Gerstl
Attorney, Agent, or Firm—Sprung, Horn, Kramer & Woods

[57] ABSTRACT

Substituted acetanilides of the formula

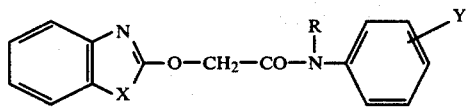

in which
X is an oxygen atom or a sulfur atom,
Y is an alkylthio group having 1 to 4 carbon atoms, and
R is an alkyl group having 1 to 4 carbon atoms, which possess herbicidal activity.

10 Claims, No Drawings

HERBICIDALLY ACTIVE NOVEL BENZAZOL-2-YLOXYACETANILIDES

The invention relates to certain new substituted acetanilides, to a process for their production and to their use as herbicides.

It has already been disclosed in Japanese laid-open Patent Application No. 154762/1979 (corresponding to U.S. Ser. No. 35361) that herbicidal activity is possessed by certain substituted carboxylic acid amides of the following general formula

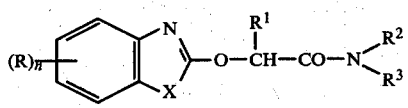
(IV)

wherein
n is 1,2,3 or 4,
each R individually represents a hydrogen atom or an alkyl, halogenoalkyl, alkoxy, halogenoalkoxy, alkylthio, halogenoalkylthio, amino, alkylamino, dialkylamino, nitro, cyano or alkoxycarbonyl group, or two R groups together represent a methylenedioxy, dichloromethylenedioxy or difluoromethylenedioxy radical,
$R^1$ represents a hydrogen atom or an alkyl group,
$R^2$ and $R^3$ may be the same or different and each individually represents a hydrogen atom or an alkyl, alkenyl, alkynyl, aralkyl, cycloalkyl, aryl or nitrogen-containing heterocyclic group which may optionally be substituted, or $R^2$ and $R^3$ together with the nitrogen atom to which they are attached form a substituted or unsubstituted, optionally partially unsaturated, and optionally benzo-fused, monocyclic or dicyclic group which may further contain one or more hetero atoms, and
X represents oxygen or sulfur.

However the herbicidal properties of these compounds are not always satisfactory from the point of view of level of action and specificity.

The present invention now provides, as new compounds, the substituted acetanilide compounds of the general formula

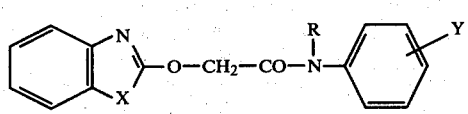
(I)

in which
X represents an oxygen atom or a sulfur atom,
Y represents an alkylthio group having 1 to 4 carbon atoms, and
R represents an alkyl group having 1 to 4 carbon atoms.

According to the present invention we provide a process for the production of a compound of the present invention, characterized in that a 2-halogenobenzazole of the general formula

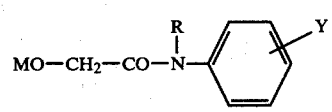
(II)

in which
X has the meaning given above and
Hal represents a halogen atom; is reacted with a compound of the general formula $$MO-CH_2-CO-N\underset{|}{\overset{R}{\phantom{N}}}-\!\!\!\!\bigcirc\!\!\!-Y \quad (III)$$

in which,
Y and R have the meanings given above and
M represents a hydrogen atom or an alkali metal atom.

It has been found that the compound of the formula (I) have an excellent activity and a broad spectrum of action. They also have a very low toxicity towards warm-blooded animals.

The compounds of the present invention have shown a markedly greater herbicidal activity than the compounds disclosed in the prior art, particularly with respect to their specificity. The present invention therefore represents an enrichment of the art.

If, for example, 2-chlorobenzothiazole and 2′-methylthio-N-methylhydroxyacetanilide are used as starting materials, the reaction according to the present invention is illustrated by the following equation:

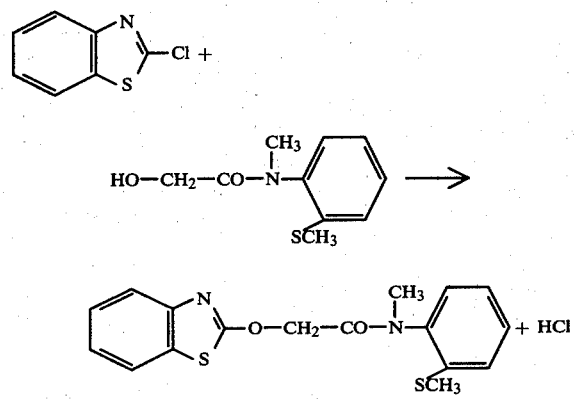

Examples of 2-halogenobenzazoles of the formula (II) which can be used as starting materials in the process of the present invention are 2-chlorobenzothiazole, and 2-chlorobenzoxazole, as well as their 2-bromo counterparts. Examples of compounds of the formula (III) which can also be used as starting materials are 2′-methylthio-N-methylhydroxyacetanilide, 2′-ethylthio-N-methylhydroxyacetanilide, 3′-methylthio-N-methylhydroxyacetanilide, 3′-propylthio-N-methylhydroxyacetanilide, and 4′-methylthio-N-methylhydroxyacetanilide, as well as their alkali metal salts.

The process of the present invention is preferably carried out in the presence of a solvent or diluent. For this purpose, any inert solvent or diluent may be employed.

Examples of such solvent and diluent are water; optionally chlorinated aliphatic, alicyclic and aromatic hydrocarbons (such as hexane, cyclohexane, petroleum ether, ligroin, benzene, toluene, xylene, methylene chloride, chloroform, carbon tetrachloride, ethylene chloride, trichloroethylene and chlorobenzene), ethers (such as diethyl ether, methyl ethyl ether, diisopropyl ether, dibutyl ether, propylene oxide, dioxane and tetrahydrofuran), ketones (such as acetone, methyl ethyl ketone, methyl isopropyl ketone and methyl isobutyl ketone), nitriles (such as acetonitrile, propionitrile and acrylonitrile, alcohols (such as methanol, ethanol, isopropanol, tert-butanol, and ethylene glycol), esters (such as ethyl acetate and amyl acetate), acid amides (such as dimethylformamide and dimethylacetamide), sulfones and sulfoxides (such as dimethylsulfoxide and sulfolane), and organic bases (such as pyridine).

Of course, a mixture of solvents and/or diluents could be used.

The process of the present invention may be carried out in the presence of an acid binding agent. Examples of such acid binding agents are alkali metal hydroxides, carbonates, bicarbonates, and alkolates and tertiary amines such as triethylamine, diethylaniline and pyridine.

The process of the present invention can be carried out over a wide range of temperatures. Generally, the reaction is carried out at a temperature of between 120° C. and the boiling point of the reaction mixture, preferably between 0° C. and 100° C. The reaction is preferably carried out under normal pressure, although it may be carried out under elevated or reduced pressure.

The active compounds according to the invention influence plant growth and can therefore be used as defoliants, desiccants, agents for destroying broadleaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The compounds of the present invention are very effective when used to combat weeds occurring in paddy field and show substantially no phytotoxicity to the rice plants being cultivated. The compounds can be used before, during and after emergence of the weeds. They can be applied, for example to the soil and/or to the stems and leaves of the weeds.

As examples of paddy-field weeds there may be mentioned, *Rotala indica, Lindernia procumbens, Ludwiga prostrate, Potamogeton distinctus, Elatine triandra, Echinochloa cus-galli, Monochoria vaginalis, Eleocharis acicularis, Eleocharis Kuroguwai, Cyperus difformis, Cyperus serotinus, Sagittaria pygmaea, Alisma canaliculatum* and *Scirpus juncoides.*

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.001 to 100 percent by weight of active compound, preferably from 0.005 to 95 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in formulations thereof or in the use forms prepared therefrom by further dilution, such as ready-to-use solutions, suspensions, emulsions, powders, pastes and granules. They are used in the customary manner, for example by watering, spraying, atomizing, scattering or dusting.

The amount of active compound in the ready-to-use preparations can vary widely according to circumstances. However, it is in general from 0.01 to 95 percent, preferably from 0.05 to 60 percent by weight.

The active compounds can be applied after emergence of the plants, but are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 10 kg of active compound per hectare, preferably between 0.5 and 3 kg/ha.

The present invention also provides herbicidal or plant-growth regulating compositions containing as active ingredient a compound of the present invention in admixture with a solid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The following examples serve to illustrate the invention further.

PREPARATIVE EXAMPLES

Example 1

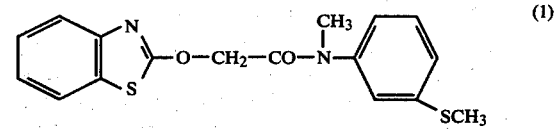

4.4 g of 85.5% potassium hydroxide was dissolved in 80 ml of isopropanol, and to this solution was added 11.51 g of 3'-methylthio-N-methylhydroxyacetanilide, followed by stirring for 30 minutes. After cooling to 0° C., 9.8 g of 2-chlorobenzothiazolo was added dropwise and the solution was stirred at room temperature for 5 hours. After this stirring, the solution was poured into 200 ml of water, and the formed crystals were recrystallized from methanol to obtain 14.4 g of the desired benzothiazol-2-yloxyacetic acid N-methyl-3-methylthioanilide, m.p. 139° to 140° C.

Example 2

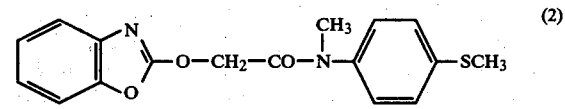

0.65 g of potassium tert-butoxide was dissolved in 10 ml of isopropanol and to this solution was added 1.0 g of 4'-methylthio-N-methylhydroxyacetanilide, followed by stirring for 30 minutes. After cooling to 0° C., 0.77 g of 2-chlorobenzoxazole was added dropwise and the solution was stirred at room temperature for 5 hours. After this stirring, the solution was poured into 50 ml of water, and extracted with ether. The ether layer was washed with water, dried on anhydrous sodium sulfate and the solvent was distilled off. The formed crystals were recrystallized from methanol to obtain 1.2 g of the desired benzoxazol-2-yloxyacetic acid N-methyl-4-methylthioanilide, m.p. 128.5° to 130° C.

In analogous manner, the compounds of the present invention shown in Table 2 were also prepared.

TABLE 1

| Compound No. | X | R | Y | Physical Constant m.p. °C. |
|---|---|---|---|---|
| 3 | O | —CH$_3$ | 2-S—CH$_3$ | 137–138 |
| 4 | S | —CH$_3$ | 2-S—CH$_3$ | 145–146 |
| 5 | O | —CH$_3$ | 3-S—CH$_3$ | 95–99 |
| 6 | S | —CH$_3$ | 4-S—CH$_3$ | 123–128 |

Compositions according to the invention are illustrated in the following examples. In these examples, the compounds according to the present invention are each identified by the number (given in brackets) from Examples 1 and 2 and Table 1 hereinabove.

Example 3

15 parts of compound (1), 80 parts of a 1:5 mixture of powdered diatomaceous earth and powdered clay, 2 parts of sodium alkylbenzenesulfonate and 3 parts of sodium alkylnaphthalenesulfonate-formalin condensate were ground and mixed together to form a wettable powder. The wettable powder is diluted with water before use.

Example 4

15 parts of compound (2), 70 parts of methyl ethyl ketone, 8 parts of polyoxyethylene alkyl phenyl ether and 7 parts of calcium alkylbenzenesulfonate were mixed by stirring to form an emulsifiable concentrate. The emulsifiable concentrate was diluted with water before use.

Example 5

2 parts of compound (3) and 98 parts of powdered clay were ground and mixed together to form a dusting agent.

Example 6

1.5 parts of compound (4), 0.5 part of isopropyl hydrogen phosphite (PAP) and 98 parts of powdered clay were ground and mixed together to form a dusting agent.

Example 7

10 parts of compound (5), 30 parts of bentonite (montmorillonite), 58 parts of talc and 2 parts of lignin sulfonate were mixed and 25 parts of water was added thereto. The mixture was intimately kneaded and finely divided by means of an extruding pelletizer to give granules of 10 to 40 mesh, which were then dried at 40° to 50° C.

Example 8

95 parts of clay particles of a size distribution of 0.2–2 mm were put into a rotary mixer and a solution of 5 parts of compound (6) was sprayed over the particles while rotating, thereby wetting the particles uniformly. They were then dried at 40° to 50° C. to form coated granules.

The herbicidal activity of the compounds of this invention is illustrated by the following biotest-example.

In this example, the compounds according to the present invention are each identified by the number (given in brackets) from Examples 1 and 2 and Table 1 hereinabove.

The known comparison compound is identified as follows:

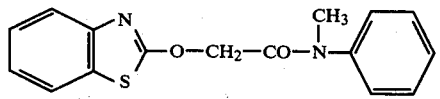

(A compound disclosed in Japanese Laid Open Patent Application No. 154762/1979)

Example 9

Test for Control Effect on Rice Field Weeds under Full Water Condition (Field Test)

Preparation of Test Compound

Using a pelletizer and a conventional pelletizing method, the following formulation was prepared and pelletized into cylindrical pellets of 0.5 mm in diameter and 1 to 3 cm in length.

| Formulation (100 parts in total) | |
|---|---|
| Active compound: | 0.8 to 10 parts |
| Polyoxyethylene alkyl phenyl ether: | 2.5 parts |
| Bentonite: | 30 parts |
| Talc: | 57.5 to 66.7 parts |

(The amount of talc corresponds to the change in amount of the active compound thereby making the total 100 parts).

Testing Methods (1) Chemical Treatment prior to Transplantation of Rice Plants The test field was plowed to a depth of 20 to 25 cm using a tractor by a conventional rice cultivating method, immediately after which, water was introduced from the irrigation channel into the field to a depth of 1 to 2 cm and the first tilling was carried out. One or two days after the first tilling, water was again introduced to a depth of about 5 cm and the last tilling was carried out. Two days after the last tilling, the test field was partitioned into 20 m² each (2 m × 10 m) using rigid plastic sheets.

Thereafter, the compound formulated as above was applied to water. Three days after the chemical application, rice seedlings grown in a nursery for this purpose (brandname: "Kinmaze", 15 days old at 2 to 2.5 leaf stage, height 15 to 17 cm) were transplanted 3 to 5 plants per root using a power-driven rice planting machine. Four weeks after the chemical application, the weed control effect was examined according to the criterion described below.

(2) Chemical Treatment after Transplantation of Rice Plants

The procedures described in Testing Method (1) were followed to the stage of the last tilling. Two days after the last tilling, the water depth of the test field was adjusted to 2 to 3 cm, and rice plants were transplanted in a manner similar to that described in Testing Method (1) using a power-driven rice planting machine, immediately after which, the field was partitioned into 20 m² each (2 m × 10 m) using rigid plastic sheets and then the water depth of the field was kept 3 to 5 cm for an extended time. Seven days after the transplantation of rice plants, the compound formulated as above was applied to water. Four weeks after the chemical application, the control effect was examined according to the following criterion.

The evaluation of the control effect is expressed as the percent weed kill relative to that in the non-treated area as follows:

5: 95% or more (100% = total destruction)
4: 80% or more but less than 95%
3: 50% or more but less than 80%
2: 30% or more but less than 50%
1: 10% or more but less than 30%
0: less than 10% (no effect)

The rate "0" in the column of the phytotoxicity towards rice plants means the absence of phytotoxicity. The results of the tests are shown in Table 2.

TABLE 2

| Compound | Amount of active ingredient kg/ha | Treatment 3 days before transplantation Weed Control Effect Weed | | | | | | | Phyto-toxicity Rice | Treatment 7 days after transplantation Weed Control Effect Weed | | | | | | | Phyto-toxicity Rice |
|---|---|---|---|---|---|---|---|---|---|---|---|---|---|---|---|---|---|
| | | A | B | C | D | E | F | G | | A | B | C | D | E | F | G | |
| (1) | 1.0 | 5 | 5 | 5 | 5 | 5 | 5 | 5 | 0 | 5 | 5 | 5 | 5 | 5 | 5 | 5 | 0 |
| (2) | " | 5 | 5 | 5 | 5 | 5 | 5 | 5 | 0 | 5 | 5 | 5 | 5 | 5 | 5 | 5 | 0 |
| (3) | " | 5 | 5 | 5 | 5 | 5 | 5 | 5 | 0 | 5 | 5 | 5 | 5 | 5 | 5 | 5 | 0 |
| (4) | " | 5 | 5 | 5 | 5 | 5 | 5 | 5 | 0 | 5 | 5 | 5 | 5 | 5 | 5 | 5 | 0 |
| (5) | " | 5 | 5 | 5 | 5 | 5 | 5 | 5 | 0 | 5 | 5 | 5 | 5 | 5 | 5 | 5 | 0 |
| (6) | " | 5 | 5 | 5 | 5 | 5 | 5 | 5 | 0 | 5 | 5 | 5 | 5 | 5 | 5 | 5 | 0 |
| IV-1 | 1.0 | 3 | 4 | 3 | 2 | 0 | 4 | 2 | 0 | 3 | 3 | 3 | 2 | 0 | 4 | 1 | 0 |

Notes: The symbols A, B, C, D, E, F and G in the column headed "Weed" denote weeds as follows:
A: *Panicum crusgalli*,
B: *Scirpus juncoides* Roxbough var.,
C: *Monochoria vaginalis* Presl,
D: Broadleaf weeds (Lindernia Procumbens Philcox, *Rotala indica* Koehne, *Elatine triandra* Schk etc.)
E: *Sagittaria pygmaea* Miq.,
F: *Eleocharis acicularis* L.
G: *Cyperus serotinus* Rottboel.

It will be understood that the specification and examples are illustrative but not limitative of the present invention and that other embodiments within the spirit and scope of the invention will suggest themselves to those skilled in the art.

We claim:

1. A substituted acetanilide of the formula:

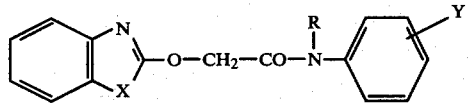

in which
X is an oxygen atom or a sulfur atom,
Y is an alkylthio group having 1 to 4 carbon atoms, and
R is an alkyl group having 1 to 4 carbon atoms.

2. A compound according to claim 1, wherein such compound is benzothiazol-2-yloxyacetic acid N-methyl-3-methylthioanilide of the formula

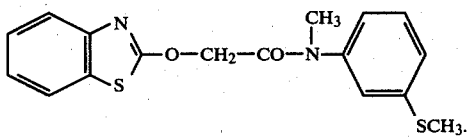

3. A compound according to claim 1, wherein such compound is benzoxazol-2-yloxyacetic acid N-methyl-4-methylthioanilide of the formula

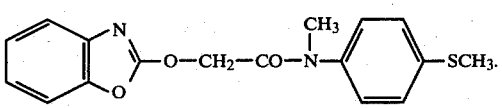

4. A compound according to claim 1, wherein such compound is benzoxazol-2-yloxyacetic acid N-methyl-2-methylthioanilide of the formula

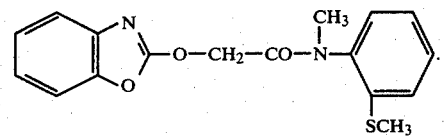

5. A compound according to claim 1, wherein such compound is benzothiazol-2-yloxyacetic acid N-methyl-2-methylthioanilide of the formula

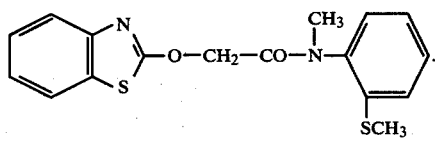

6. A compound according to claim 1, wherein such compound is benzoxazol-2-yloxyacetic acid N-methyl-3-methylthioanilide of the formula

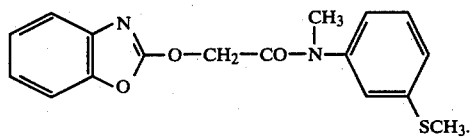

7. A compound according to claim 1, wherein such compound is benzothiazol-2-yloxyacetic acid N-methyl-4-methylthioanilide of the formula

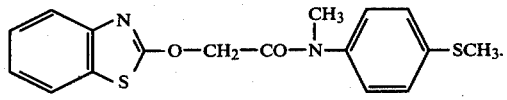

8. A herbicidal composition comprising a herbicidally effective amount of a compound according to claim 1 in admixture with a diluent.

9. A method of combating weeds comprising applying to the weeds, or to a habitat thereof, a herbicidally effective amount of a compound according to claim 1.

10. The method according to claim 9, wherein to a rice field there is applied
benzothiazol-2-yloxyacetic acid N-methyl-3-methylthioanilide,
benzoxazol-2-yloxyacetic acid N-methyl-4-methylthioanilide,
benzoxazol-2-yloxyacetic acid N-methyl-2-methylthioanilide,
benzothiazol-2-yloxyacetic acid N-methyl-2-methylthioanilide,
benzoxazol-2-yloxyacetic acid N-methyl-3-methylthioanilide or
benzothiazol-2-yloxyacetic acid N-methyl-4-methylthioanilide.

* * * * *